(12) United States Patent
Seltzer et al.

(10) Patent No.: US 10,527,565 B2
(45) Date of Patent: Jan. 7, 2020

(54) NMR SENSOR FOR ANALYZING CORE OR FLUID SAMPLES FROM A SUBSURFACE FORMATION

(71) Applicant: Chevron U.S.A. Inc., San Ramon, CA (US)

(72) Inventors: Scott Jeffrey Seltzer, Houston, TX (US); Haijing Wang, Sugar Land, TX (US); Boqin Sun, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 1115 days.

(21) Appl. No.: 14/811,906

(22) Filed: Jul. 29, 2015

(65) Prior Publication Data
US 2017/0030845 A1    Feb. 2, 2017

(51) Int. Cl.
*G01N 24/08* (2006.01)
*G01R 33/383* (2006.01)
*G01V 3/14* (2006.01)
G01R 33/3875 (2006.01)
G01R 33/44 (2006.01)

(52) U.S. Cl.
CPC ......... *G01N 24/081* (2013.01); *G01R 33/383* (2013.01); *G01V 3/14* (2013.01); *G01R 33/3875* (2013.01); *G01R 33/448* (2013.01)

(58) Field of Classification Search
CPC .. G01V 3/14; G01R 33/20; G01R 33/44–586; G01N 24/08–088
See application file for complete search history.

(56) References Cited

U.S. PATENT DOCUMENTS

| 5,095,271 | A | 3/1992 | Ohkawa |
| 6,072,251 | A * | 6/2000 | Markle ............... G03F 7/70758 310/12.05 |
| 6,111,408 | A | 8/2000 | Blades et al. |
| 6,346,813 | B1 | 2/2002 | Kleinberg |
| 6,441,514 | B1 * | 8/2002 | Markle ............... G03F 7/70758 310/12.06 |
| 6,737,864 | B2 | 5/2004 | Prammer et al. |
| 6,803,761 | B2 | 10/2004 | Prammer et al. |

(Continued)

FOREIGN PATENT DOCUMENTS

| CN | 201359896 Y | 12/2009 |
| GB | 2398876 A | 9/2004 |

(Continued)

OTHER PUBLICATIONS

Caprihan, A., et al.; "Flow Measurements by NMR"; Physics Reports (Review Section of Physics Letters), vol. 198, No. 4, 1990, pp. 195-235.

(Continued)

*Primary Examiner* — Huy Q Phan
*Assistant Examiner* — David B Frederiksen

(57) ABSTRACT

A sensor and a method are disclosed for analyzing fluid and/or rock samples from a subsurface formation. Embodiments of the sensor and method utilize an array of magnets arranged in a specific way. The array and its arrangement may allow for NMR analysis of multiple samples or analysis of fluid samples which were not possible with existing technology. Further details and advantages of various embodiments of the method are described in more detail herein.

31 Claims, 13 Drawing Sheets

(56) References Cited

U.S. PATENT DOCUMENTS

| | | | |
|---|---|---|---|
| 6,825,657 B2 | 11/2004 | Kleinberg et al. | |
| 6,841,996 B2 | 1/2005 | Madio et al. | |
| 6,891,369 B2 | 5/2005 | Hurlimann et al. | |
| 6,940,378 B2 | 9/2005 | Miller et al. | |
| 7,061,237 B2 | 6/2006 | Pines et al. | |
| 7,205,764 B1* | 4/2007 | Anderson | G01R 33/282 324/307 |
| 7,532,007 B2 | 5/2009 | Song et al. | |
| 7,932,720 B2 | 4/2011 | James et al. | |
| 8,009,001 B1 | 8/2011 | Cleveland | |
| 8,952,691 B2 | 2/2015 | Blmich et al. | |
| 2002/0075000 A1 | 6/2002 | Prammer et al. | |
| 2002/0188380 A1* | 12/2002 | Ross | B62D 57/024 700/245 |
| 2009/0121712 A1* | 5/2009 | Han | G01R 33/282 324/307 |
| 2009/0128272 A1 | 5/2009 | Hills | |
| 2010/0085048 A1* | 4/2010 | Bouchard | G01R 33/48 324/307 |
| 2010/0090698 A1* | 4/2010 | Blumich | G01N 24/08 324/309 |
| 2011/0001474 A1 | 1/2011 | Miller et al. | |
| 2011/0133872 A1* | 6/2011 | Souder | H01F 7/0294 335/306 |
| 2011/0150779 A1 | 6/2011 | Han et al. | |
| 2013/0009735 A1 | 1/2013 | Nath et al. | |
| 2013/0325408 A1 | 12/2013 | Song | |
| 2014/0084927 A1* | 3/2014 | Walsh | G01N 24/081 324/319 |
| 2014/0312901 A1 | 10/2014 | Chen et al. | |
| 2014/0353971 A1* | 12/2014 | Davey | F03B 11/06 290/52 |
| 2015/0061670 A1 | 3/2015 | Fordham et al. | |
| 2015/0177343 A1 | 6/2015 | Wald et al. | |
| 2015/0300968 A1* | 10/2015 | Bae | G01N 24/088 506/6 |
| 2015/0338750 A1* | 11/2015 | Yang | G03F 7/70758 355/72 |
| 2016/0011328 A1* | 1/2016 | Jones | G01N 33/2823 324/303 |
| 2016/0123971 A1* | 5/2016 | Taicher | G01N 24/08 436/501 |
| 2016/0212546 A1* | 7/2016 | Salvatti | H04R 9/06 |

FOREIGN PATENT DOCUMENTS

| | | |
|---|---|---|
| WO | 2007/120057 A1 | 10/2007 |
| WO | 2009029241 A1 | 3/2009 |
| WO | 201000433 A1 | 9/2010 |
| WO | 2012103397 A2 | 8/2012 |
| WO | 2014171976 A1 | 10/2014 |

OTHER PUBLICATIONS

Hoult, D.I.; "Fast Recovery, High Sensitivity NMR Probe and Preamplifier for Low Frequencies"; Rev. Sci. Instrum., vol. 50, No. 2, Feb. 1979, pp. 193-200.

Moule, Adam J., et al.; "Amplification of Xenon NMR and MRI by Remote Detection"; Proceedings of the National Academy of Sciences, Aug. 5, 2003, vol. 100, No. 16, pp. 9122-9127.

Straley, Christian, et al.; "Core Analysis by Low-Field NMR"; The Log Analyst, vol. 38 Mar.-Apr. 1997, pp. 84-95.

Anferova, et al.; "Improved Halbach Sensor for NMR Scanning of Drill Cores"; Magnetic Resonance Imaging, Elsevier Science, (May 4, 2007), vol. 25, No. 4, pp. 474-480.

Cooley, Clarissa Zimmerman, et al.; "Two-Dimensional Imaging in a Lightweight Portable MRI Scanner without Gradient Coils"; Magnetic Resonance in Medicine, (Mar. 25, 2014), vol. 73, No. 2, pp. 872-883.

International Search Report, dated Nov. 24, 2016, during the prosecution of International Application No. PCT/US2016/042429.

International Preliminary Report on Patentability, dated Jan. 30, 2018, during the prosecution of International Application No. PCT/US2016/042429.

* cited by examiner

NMR SENSOR FOR ANALYZING CORE OR FLUID SAMPLES FROM A SUBSURFACE FORMATION

CROSS-REFERENCE TO RELATED APPLICATIONS

Not applicable.

STATEMENT REGARDING FEDERALLY SPONSORED RESEARCH OR DEVELOPMENT

Not applicable

BACKGROUND

Field of the Invention

This invention relates generally to the field of geological exploration for hydrocarbons. More specifically, the invention relates to an NMR sensor and a method of analyzing samples from a subsurface formation.

Background of the Invention

Nuclear magnetic resonance (NMR) is a powerful tool for analysis of rock core samples extracted from underground formations during oil and gas exploration and production. NMR is sensitive to water and hydrocarbons, but insensitive to the rock matrix, providing a porosity measurement that includes only the fluid in the pore spaces. It can also be used to characterize the mixture of fluids present in the sample as extracted, including both bound and free water, and different molecular weights of both live and dead oil. NMR also provides a non-destructive method for measuring the pore size distribution of the sample, unlike mercury injection methods which contaminate the sample.

NMR core measurements are conducted using "low-field" devices that typically apply a static magnetic field on the order of 500 Gauss (G) to the sample, yielding an NMR measurement frequency on the order of 2 MHz for hydrogen nuclei (similar to the measurement frequency of NMR logging tools). Such fields can be generated using arrays of permanent magnets. For comparison, "high-field" magnetic resonance devices common in medical and chemistry applications typically apply a static field in the range of 10,000 G to more than 200,000 G, for frequencies of 40 MHz to more than 1 GHz; it is generally not possible to achieve such field strength using permanent magnets, and so these fields can only be sustained using superconducting coils. (Electromagnets can be used for fields up to about 30,000 G.) Low-field measurements are preferred for rock analysis because they are more easily correlated with logging data, because low-field devices are significantly less expensive both to purchase and to maintain, and because strong magnetic fields introduce unacceptable susceptibility artifacts caused by distortions of the field at the surface of the rock matrix (such as at the rock-pore boundaries).

One problem with current devices is the lack of parallelism; samples are analyzed one at a time, and multiple scans (for purposes of signal averaging) generally require a low duty cycle because of the long repolarization time of the nuclear spins in the sample. It could potentially be much more efficient to use a device that can be loaded with multiple samples and analyze them in parallel.

Consequently, there is a need for improved methods and tools to use NMR for analyzing rock core or fluid samples from potential or existing hydrocarbon-bearing subsurface formations.

BRIEF SUMMARY

A sensor and a method are disclosed for analyzing fluid and/or rock samples from a subsurface formation. Embodiments of the sensor and method utilize one or more arrays of magnets arranged in a specific way. The magnet arrays may each also include a corresponding array of radiofrequency (RF) circuits and electronics. The arrays and their arrangement may allow for NMR analysis of multiple samples or analysis of fluid samples which were not possible with existing technology. Further details and advantages of various embodiments of the method are described in more detail herein.

In an embodiment, a nuclear magnetic resonance (NMR) sensor comprises a plurality of magnet arrays. Each magnet array comprises a plurality of magnets arranged in a semi-Halbach configuration. The semi-Halbach configuration produces a magnetic field both inside and outside of the array. The magnetic field distribution inside the array comprises a sweet spot, and the magnets are non-contiguous to one another.

In another embodiment, a system for using nuclear magnetic resonance (NMR) to analyze a core or fluid sample from a subsurface formation comprises a plurality of magnet arrays. Each magnet array comprises a plurality of magnets arranged in a semi-Halbach configuration. The semi-Halbach configuration produces a magnetic field both inside and outside of the array. The magnetic field distribution inside the array comprises a sweet spot, and the magnets are non-contiguous to one another. The system also comprises an interface for receiving one or more user inputs. The system additionally comprises a memory resource. Moreover, the system comprises input and output functions for presenting and receiving communication signals to and from a human user. The system also comprises one or more central processing units for executing program instructions coupled to the NMR sensor and configured to receive one or more signals from the NMR sensor; and program memory, coupled to the central processing unit, for storing a computer program including program instructions that, when executed by the one or more central processing units, cause the system to perform a plurality of operations for analyzing a fluid or core sample from a subsurface formation.

In an embodiment, a method of using nuclear magnetic resonance (NMR) to analyze a sample from a subsurface formation comprises disposing a sample extracted from a subsurface formation within an NMR sensor. The NMR sensor comprises one or more magnet arrays. Each magnet array comprises a plurality of magnets arranged in a semi-Halbach configuration. The semi-Halbach configuration produces a magnetic field both inside and outside of the array. The magnetic field distribution inside the array comprises a sweet spot. The magnets are non-contiguous to one another. The method further comprises using the NMR sensor to analyze the sample.

In another embodiment, a method of using nuclear magnetic resonance (NMR) to analyze a fluid sample from a subsurface formation comprises flowing a fluid sample extracted from a subsurface formation through an NMR sensor. The NMR sensor comprises one or more magnet arrays. Each magnet array comprises a plurality of magnets arranged in a semi-Halbach configuration. The semi-Halbach configuration produces a magnetic field both inside and outside of the array. The magnetic field distribution inside the array comprises a sweet spot. The magnets are non-contiguous to one another. The method also comprises using the NMR sensor to analyze the fluid sample.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

DETAILED DESCRIPTION OF THE PREFERRED EMBODIMENTS

Referring now to the Figures, embodiments of the disclosed sensor and methods will be described. As a threshold matter, embodiments of the sensor and methods may be implemented in numerous ways, as will be described in more detail below, including for example as a system (including a computer processing system), a method (including a computer implemented method), an apparatus, a computer readable medium, a computer program product, a graphical user interface, a web portal, or a data structure tangibly fixed in a computer readable memory. Several embodiments of the disclosed sensor and methods are discussed below. The appended drawings illustrate only typical embodiments of the disclosed methods and therefore are not to be considered limiting of its scope and breadth.

Figure 1A:
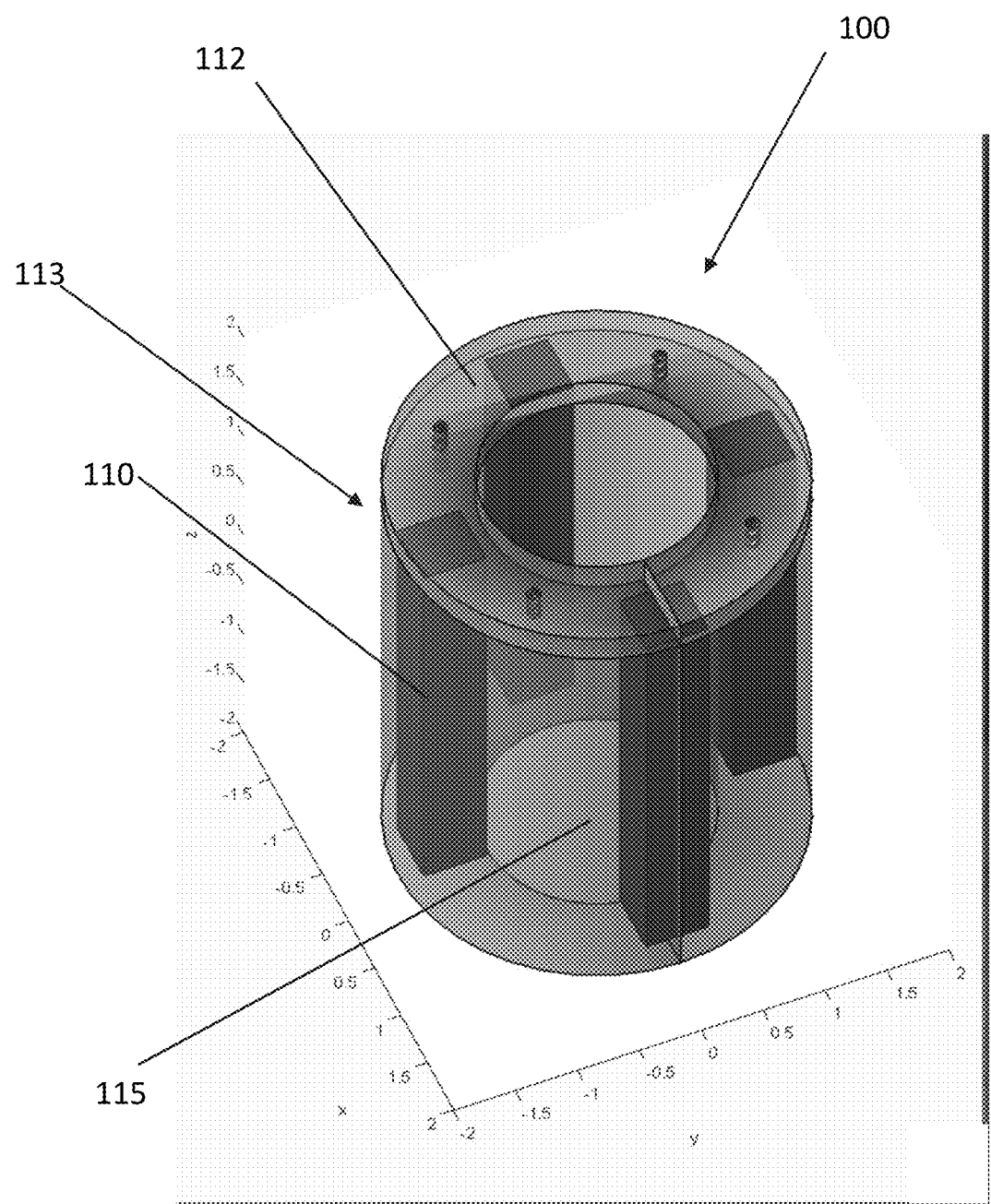
FIG. 1A illustrates an embodiment of an NMR sensor for analyzing samples from a subsurface formation.
Figure 1B:
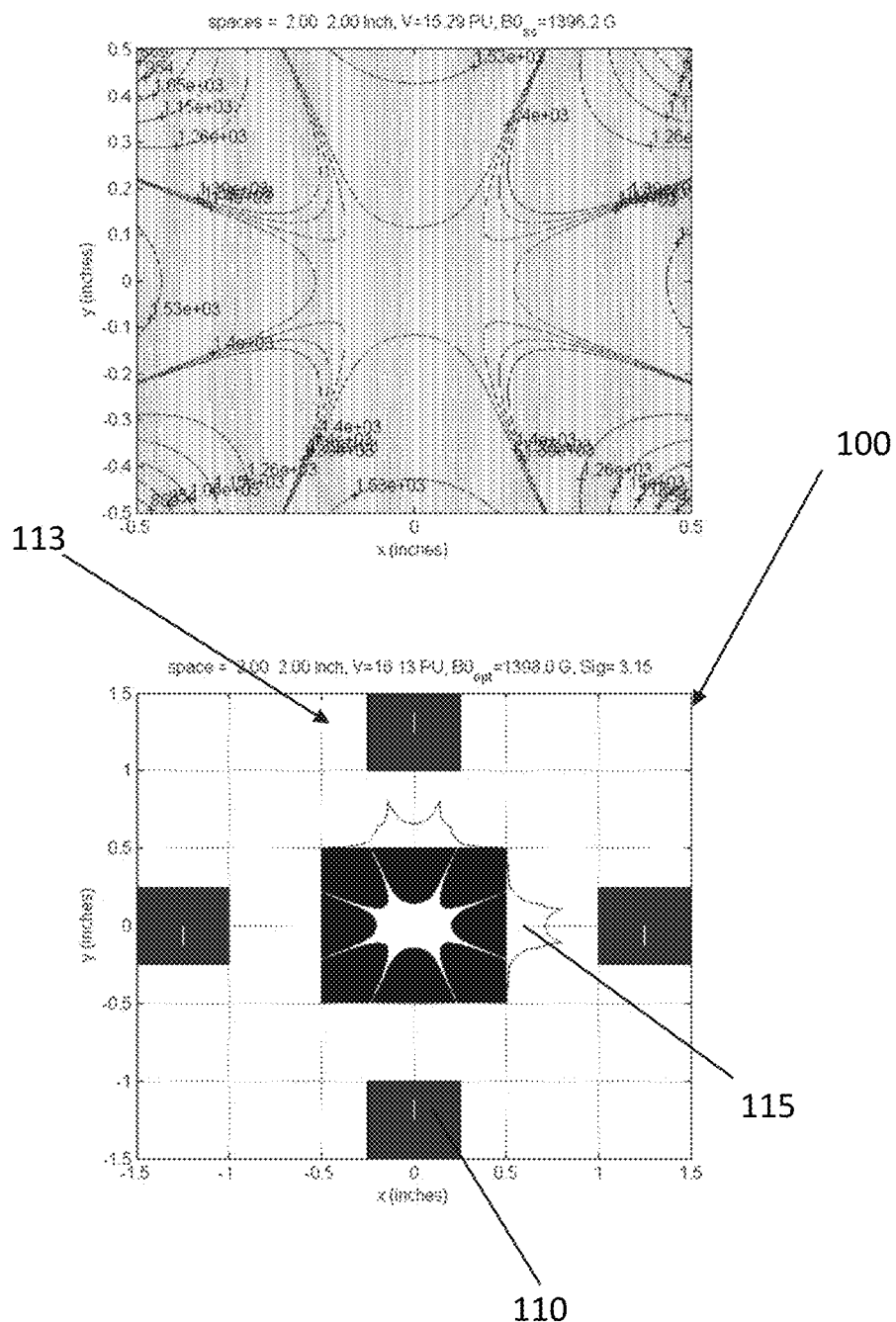
FIG. 1B illustrates an example of a "sweet spot" from an embodiment of an NMR sensor for analyzing samples from a subsurface formation.

For purposes of this disclosure, embodiments of the tool may be referred to as the MultiSPOT (or NMR MultiSPOT), for Multiple Semi-Halbach Porosity Tool. Generally, embodiments of the tool 100 include a plurality of magnets 110 arranged in an array 113. In an embodiment, referring to FIGS. 1A-1B, the array 113 may be composed of several permanent magnets 110, arranged so as to produce a "sweet spot" 115 within the array 113. The magnets 110 may be any suitable magnet known to those of skill in the art. In an embodiment, the magnets can be permanent magnets. More specifically, examples of permanent magnets include without limitation, neodymium magnets, rare earth magnets, ceramic magnets, iron alloy magnets, or combinations thereof. In an embodiment, magnets 110 may be cuboidal in geometry. However, other suitable geometries may be used. For example, in some embodiments, magnets 110 may be cylindrical. In an embodiment, magnets 110 may have a length to height ratio of 1:1, alternatively 2:1, alternatively 3:1. The magnets 110 may range in strength from 0.1 to 1.6 T. However, any strength magnet may be used. In the embodiment shown in FIG. 1A, the magnets 110 may be held in place by support elements 112 which in some embodiments may be coupled to magnets 110. Support elements 112 may be metallic yet non-magnetic, or alternatively polymeric, ceramic, or plastic. As used herein, the "sweet spot" 115, as shown in FIG. 1B, refers to the region within the array 113, distributed around the local extremum in the magnetic field strength, where the magnetic field is most uniform and so the largest volume of spins can be excited and detected simultaneously. Although shown in the center of the array 113 in the Figures, the sweet spot 115 may be located in any position within the array 113 according to the configuration of magnets 110. The core or fluid samples to be analyzed are generally disposed or placed in the sweet spots 115 for analysis. To be clear, samples of any suitable phase may be analyzed (e.g. solid, fluid, etc.) with embodiments of the sensor. Core or fluid samples from a subsurface formation (which may or may not contain hydrocarbons) may be extracted from the subsurface formation through any methods known to those of skill in the art.

For purposes of this disclosure, this arrangement may be hereinafter referred to as a semi-Halbach arrangement because it resembles a Halbach cylinder. However, embodiments of the semi-Halbach arrangement or array differ in several ways and are not to be equated with a Halbach cylinder which is known in the art. For example, the typical Halbach cylinder is composed of a contiguous ring of magnetic material, and the design generally used for NMR purposes produces an extremely homogeneous magnetic field in its center, with almost no field outside. That is, the sweet spot is effectively most (if not all) of the internal volume of the Halbach cylinder. Furthermore, standard NMR Halbach cylinders need to be equipped with extra coils for applying gradients, and the amplitude of the gradient will generally be much smaller (compared to the inherent gradient of the semi-Halbach) due to limitations on electrical currents in the coils. In comparison, the semi-Halbach configuration as disclosed herein is both simpler and cheaper, and it creates a sweet spot that features a relatively strong magnetic field gradient that can be exploited for NMR measurements of diffusion. For NMR rock analysis, the high field homogeneity of the standard Halbach may in fact be a disadvantage.

An NMR measurement is sensitive to the volume wherein the spread of resonance frequencies of the target nuclear species overlaps with the measurement bandwidth; the bandwidth is determined by the excitation pulse design and the electronics hardware, while the resonance frequency distribution is determined by the magnetic field distribution. For the semi-Halbach configuration, the magnetic field distribution is designed to give a large "sweet spot" volume where the resonance frequencies fall within a reasonable measurement bandwidth, providing a large sensitive region. Embodiments of the semi-Halbach design may actually decrease sensitive volume for the sake of a higher built-in field gradient. Also in addition, the semi-Halbach configuration produces a magnetic field both on the inside and outside of the array 113, unlike a traditional Halbach cylinder, and embodiments of the MultiSPOT take advantage of this feature.

As seen in FIGS. 1-9, an embodiment of NMR sensors or MultiSPOTs may include a pattern of semi-Halbach arrays 113, with each array 113 sharing magnets 110 with those adjacent to it. For example, as shown in FIG. 1C, each array 113 has 4 magnets with a sweet spot 115. However, each array 113 shares magnets 110 with the other arrays 113. Magnets 110 are generally disposed non-contiguous to one another. That is, they are not in contact with one another. In this way, multiple sweet spot regions 115 are produced using a minimal number of magnets. In the exemplary embodiments shown in FIGS. 2 through 7 and FIG. 9 the magnets simulated had dimensions of 0.5 inches×0.5 inches×2 inches with remnant magnetization of 1.48 Tesla. However, as discussed already, the magnets 110 may be of any suitable dimension, shape, or strength. The magnets 110 in each array 113 can be arranged in any pattern that fully tiles, or "tessellates", the plane with the sweet spots occurring in the center of individual groups of magnets. Any number of patterns may be incorporated into the sensor 100. In one embodiment, the patterns can be made up of regular polygons (i.e. equiangular and equilateral in geometry). Examples of regular polygons include without limitation, squares, triangles, hexagons, pentagons, octagons, decagons, any regular n-gon (where n is equal to the number of sides), and combinations thereof. However it is contemplated that all designs and applications discussed in this disclosure should be considered and can be extended to all tessellating patterns. The simplest patterns may include those of three-, four-, and six-magnet arrays 113, since a plane can be fully tiled by regular triangles, squares, and hexagons (see FIGS. 3A-B, 2A-B, and 4A-B, respectively). Patterns consisting of more than one type of regular polygon are also possible, such as the two different patterns of octagons and squares shown in FIGS. 6A-B and 7A-B. In other embodiments, the arrays 113 may be made up of irregular polygons where the sides are not equilateral and/or not equiangular. In addition, magnets 110 may be spaced any suitable distance from each other in the patterns depending on the desired magnetic field (i.e. field strength and/or spatial profile) and application. Each array 113 may also include one or more coils. In an embodiment, each array 113 may also include an array of coils. In an embodiment, the coils can be radiofrequency coils, gradient coils, shimming coils, or combinations thereof. However, any coils known to those of skill in the art may be used. The purpose of the coils is to act as an antenna for transmitting and receiving radiofrequency signals into/from the sample; as well one or more coils for application of magnetic field gradients, either continuously or pulsed; as well as one or more coils for "shimming" or cancellation of existing (device or environmental) magnetic field gradients. In an embodiment, the coils can be disposed within the array 113. In some embodiments, a layer of metal, which may be referred to as an RF shield, may be positioned between the coils and the magnets, to shield (via the skin effect) the radiofrequency signals from causing eddy currents and/or mechanical ringing in the magnets.

In other embodiments of the sensor 100, the arrays 113 do not need to be arranged on the surface of a flat plane. The tiling can instead be of another two-dimensional surface, such as the surface of a sphere or polyhedron; perhaps the most well-known such tiling is that of the surface of a soccer ball by alternating regular pentagons and regular hexagons.

There are a number of different possible arrangements of the magnets in a standard Halbach cylinder to produce a variety of magnetic field distributions. The arrangement commonly used for NMR applications is an effective dipole that produces a highly uniform field inside the cylinder. Ideally, this dipole arrangement consists of magnetic material with a continuously varying magnetization that undergoes an accumulated 720° (4π) rotation over the physical 360° (2π) of the cylinder—in other words, the orientation of the magnetization varies continuously to complete two full rotations along the outside of the cylinder. In practice, discontinuous pieces of magnetic material are generally used, each with a uniform direction of magnetization. For some patterns, the magnets of the MultiSPOT array can be arranged so that each semi-Halbach array 113 features the same 4π total rotation of magnetization, giving the maximal field in each sweet spot; this is possible for the triangle and square patterns, for instance, as shown in FIGS. 3 and 2, respectively. Likewise, for the octagonal/square patterns it can be achieved for the octagonal units but not the square units. In all cases, the magnetization of all individual magnets can instead be set parallel, sacrificing the field strength in some units in favor of maintaining a more uniform field pattern among the units (compare FIGS. 4 and 5 for the case of the hexagonal pattern).

In determining the magnetic field for an array 113, consider a two-dimensional, infinite grid of magnets, each with magnetic dipole moment m, arranged around a detection region at the origin. The magnetic field experienced at the origin due to a magnet 110 located at a position $r=\hat{r}r$ is given by:

$$B(r) = \frac{\mu_0}{4\pi r^3}[3(m \cdot \hat{r})\hat{r} - m]. \qquad (1)$$

Figure 1C:
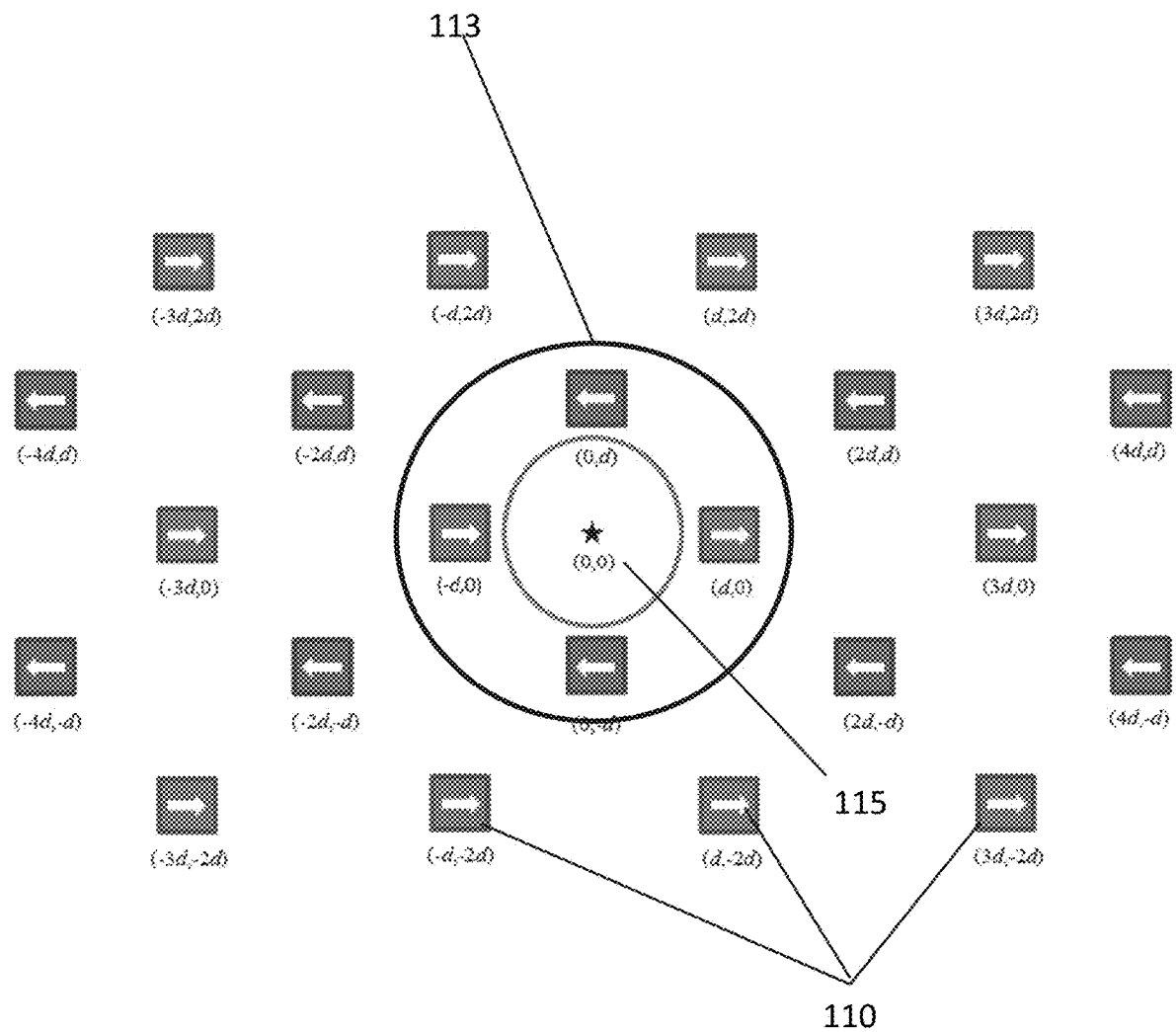
FIG. 1C illustrate a theoretical embodiment of an NMR sensor for analyzing samples from a subsurface formation. In this embodiment, the sensor includes a two-dimensional grid of magnets with a separation of 2d, with an NMR detection region at the origin.
Figure 2A:
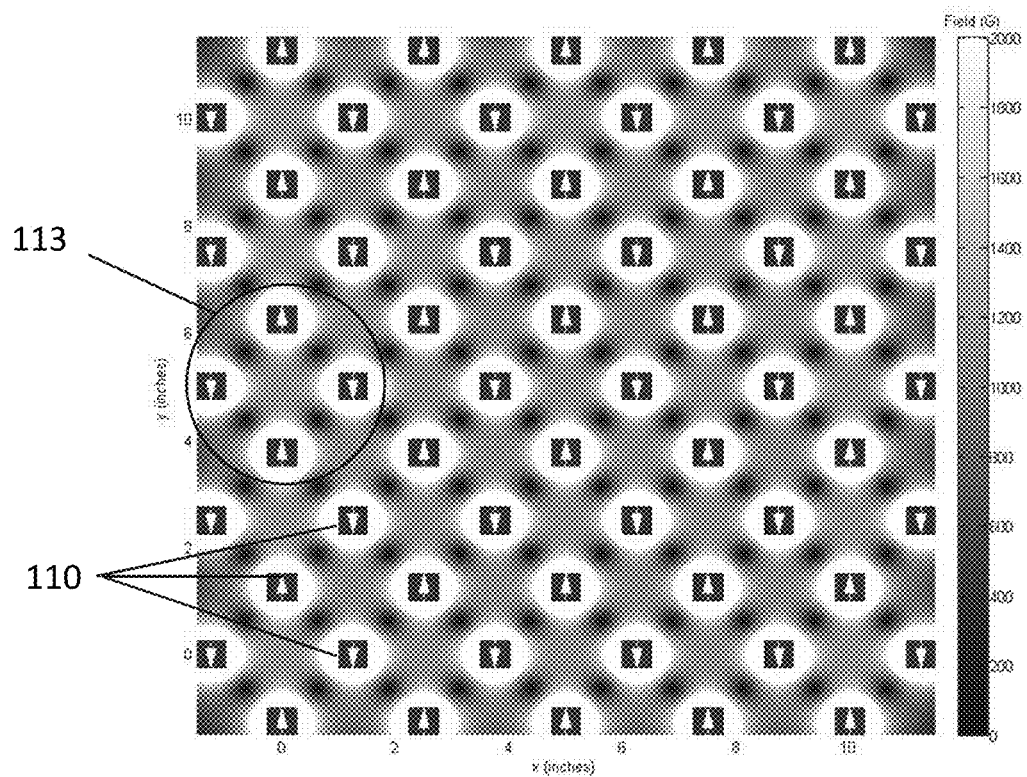
FIG. 2A illustrates a computer simulation of the magnetic field strength, B, from an embodiment of the NMR sensor with four (4) magnets per array with magnetizations oriented appropriately to maintain a 4π Halbach condition.
Figure 2B:
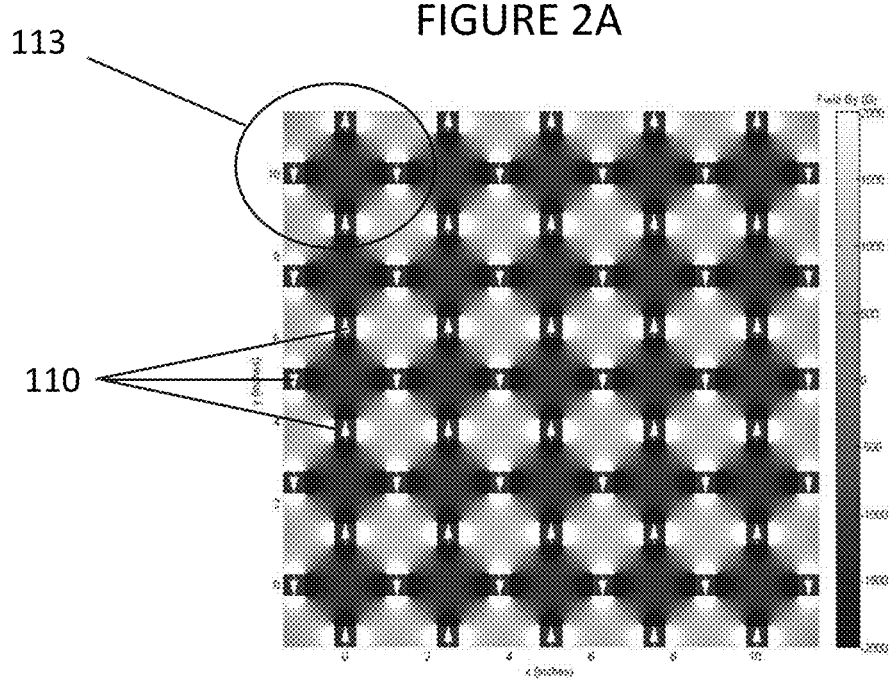
FIG. 2B illustrates a computer simulation of the magnetic field component, $B_y$, from an embodiment of the NMR sensor with four (4) magnets per array showing that the direction of the field is reversed between alternating rows/columns.
Figure 3A:
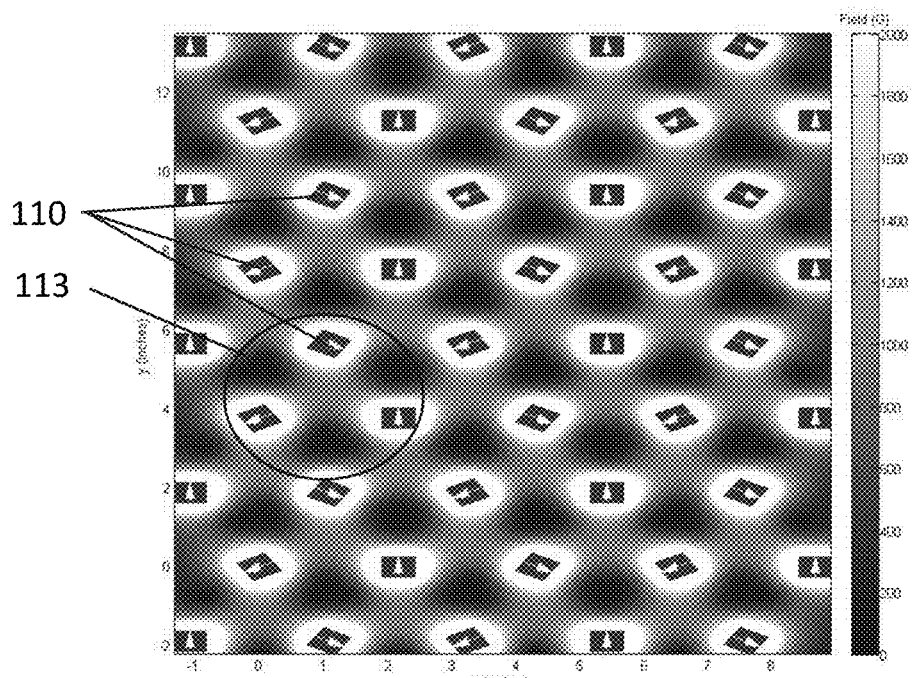
FIG. 3A illustrates a computer simulation of the magnetic field strength, B, from an embodiment of the NMR sensor with three (3) magnets per array with magnetizations oriented appropriately to maintain a 4π Halbach condition.
Figure 3B:
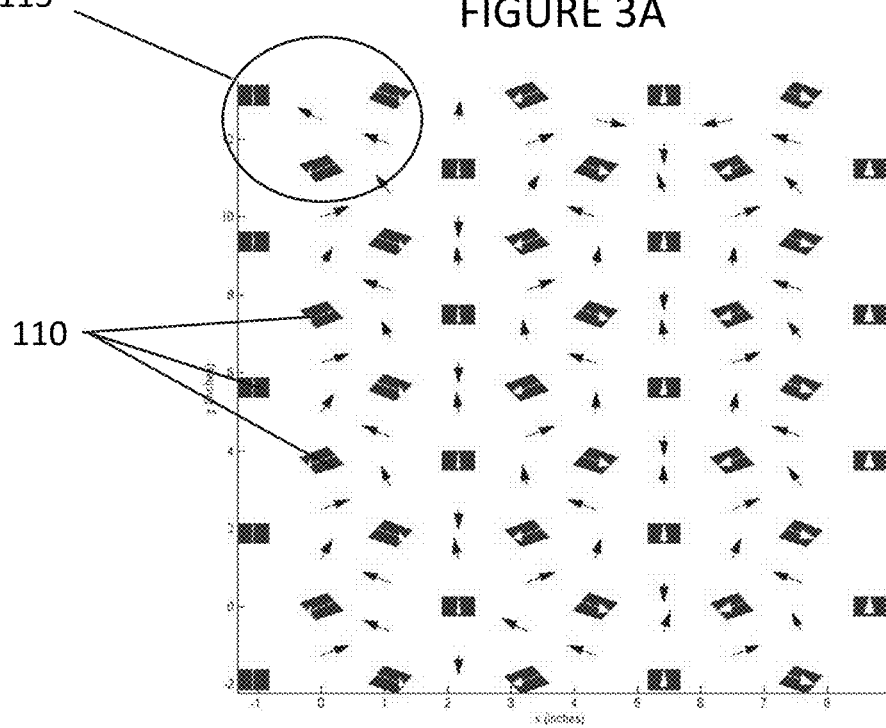
FIG. 3B illustrates direction of the magnetic field vector in the x-y plane at each sweet spot for the embodiment with three magnets per array.
Figure 4A:
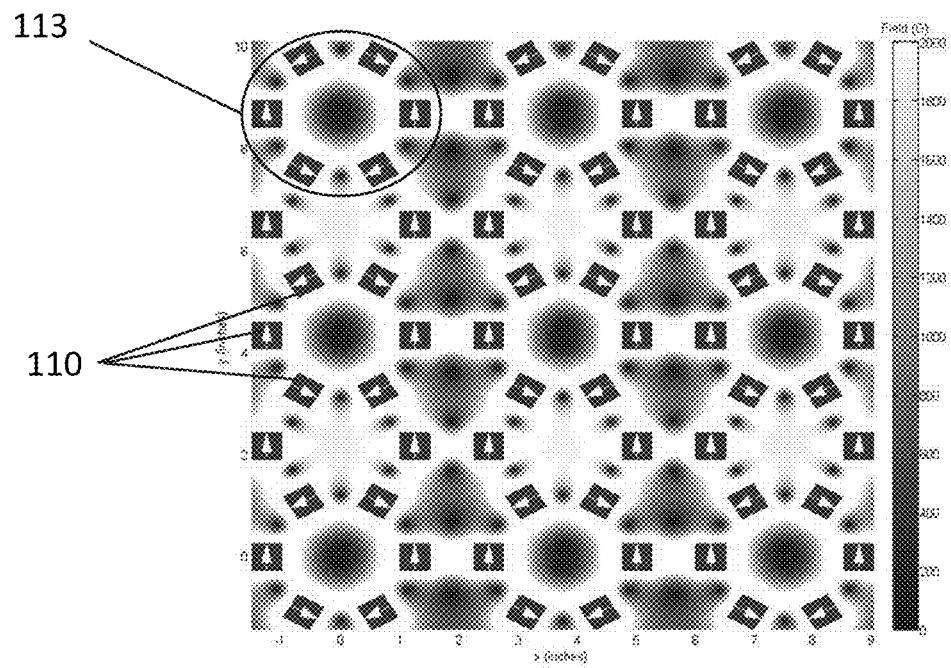
FIG. 4A illustrates a computer simulation of the magnetic field strength, B, from an embodiment of the NMR sensor with six (6) magnets per array with magnetizations oriented appropriately to maintain a 4π Halbach condition in a subset of the arrays.
Figure 4B:
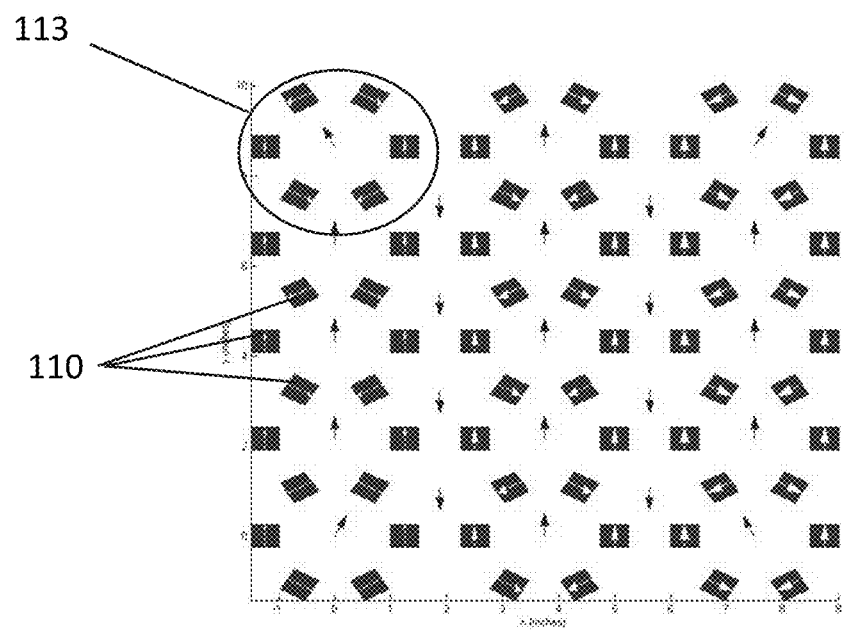
FIG. 4B illustrates a computer simulation of the direction of the magnetic field vector in the x-y plane at each sweet spot from an embodiment of the NMR sensor with six (6) magnets per array with magnetizations oriented appropriately to maintain a 4π Halbach condition in a subset of the arrays.
Figure 5A:
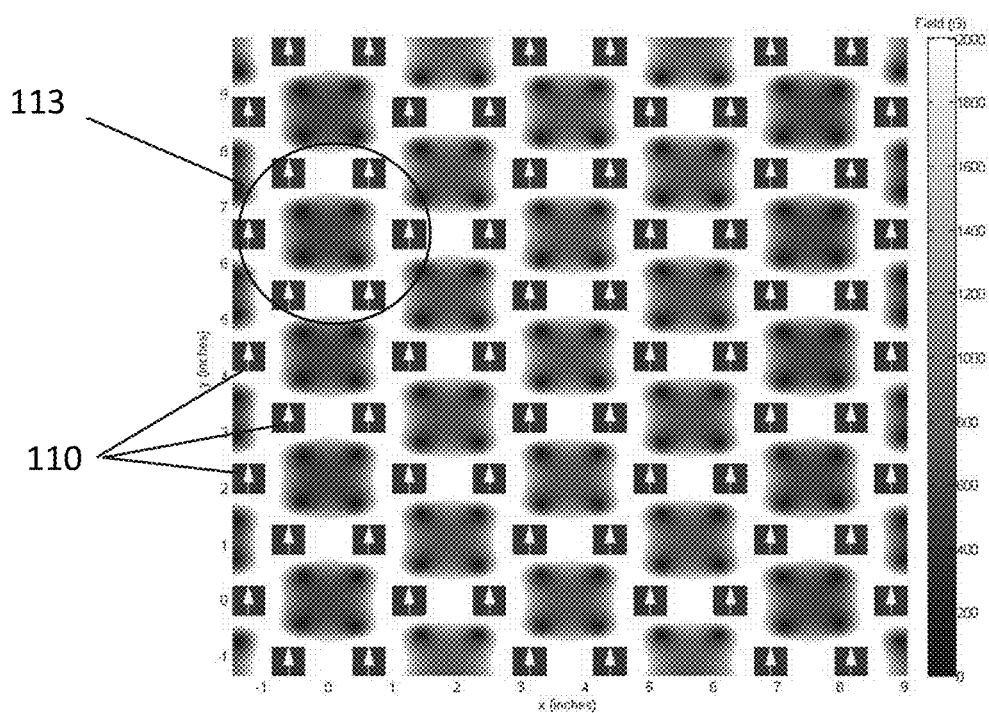
FIG. 5A illustrates a computer simulation of the magnetic field strength, B, from an embodiment of the NMR sensor with six (6) magnets per array with all magnetizations oriented parallel.
Figure 5B:
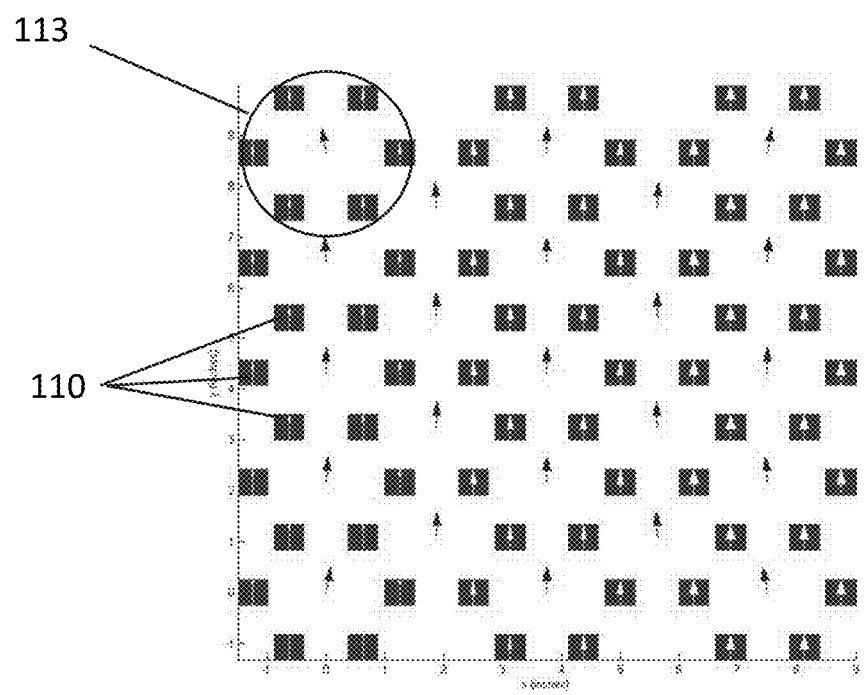
FIG. 5B illustrates a computer simulation of the direction of the magnetic field vector in the x-y plane at each sweet spot from an embodiment of the NMR sensor with six (6) magnets per array with all magnetizations oriented parallel.
Figure 6A:
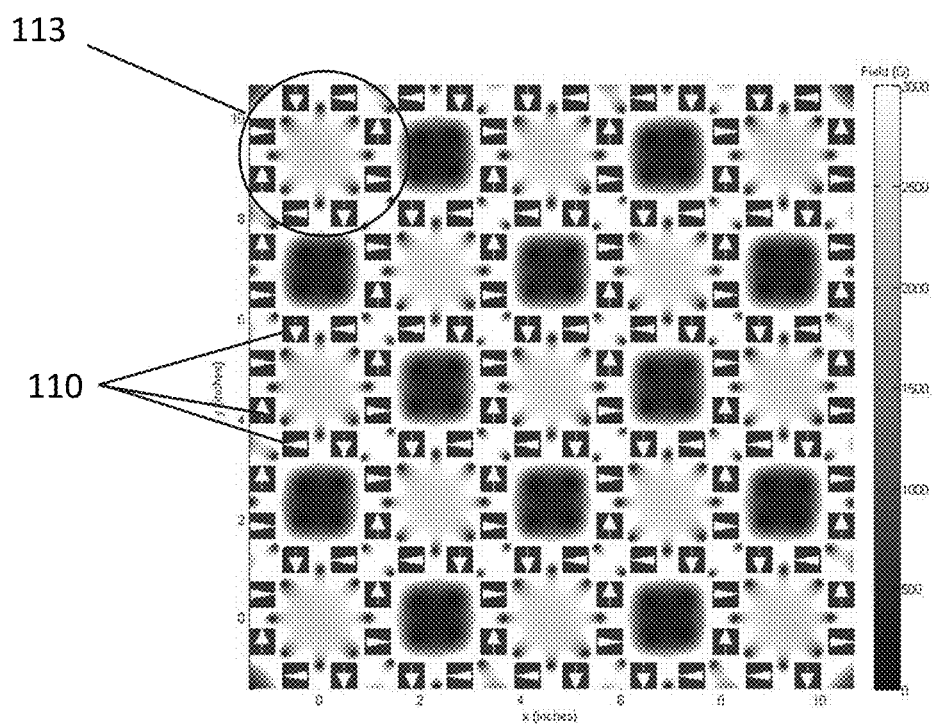
FIG. 6A illustrates a computer simulation of the magnetic field strength, B, from an embodiment of the NMR sensor with eight (8) magnets per array.
Figure 6B:
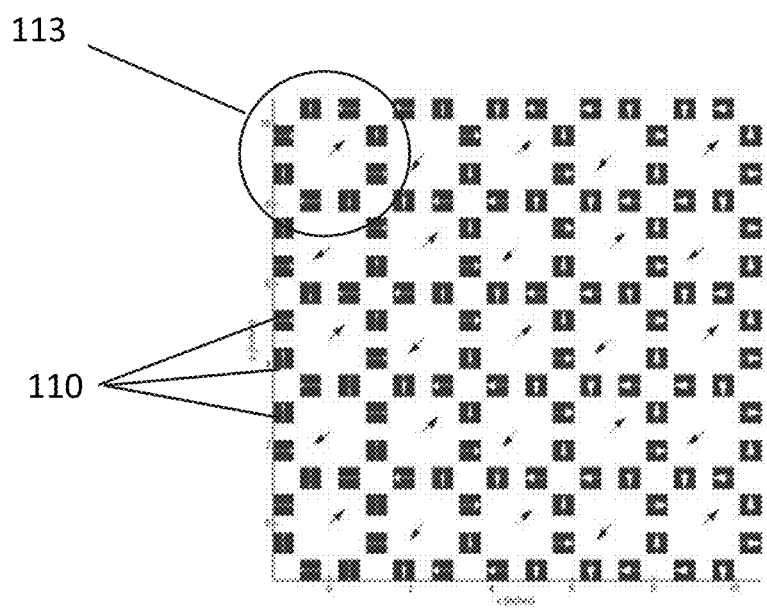
FIG. 6B illustrates a computer simulation of direction of the magnetic field vector in the x-y plane at each sweet spot from an embodiment of the NMR sensor with eight (8) magnets per array.
Figure 7A:
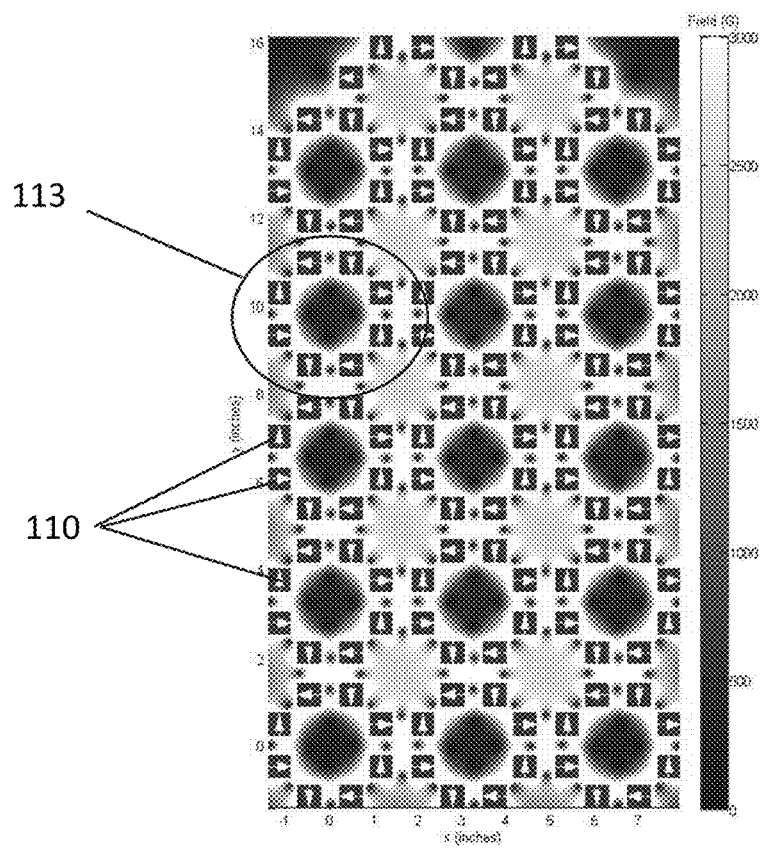
FIG. 7A illustrates a computer simulation of the magnetic field strength, B, from an embodiment of the NMR sensor with eight (8) magnets per array.
Figure 7B:
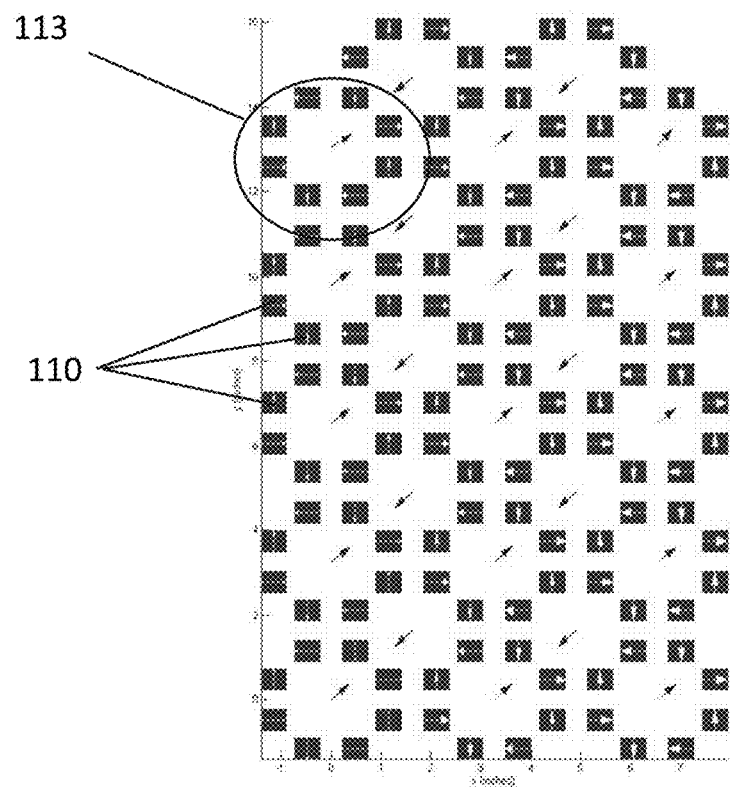
FIG. 7B illustrates a computer simulation of the direction of the magnetic field vector in the x-y plane at each sweet spot from an embodiment of the NMR sensor with eight (8) magnets per array.
Figure 8A:
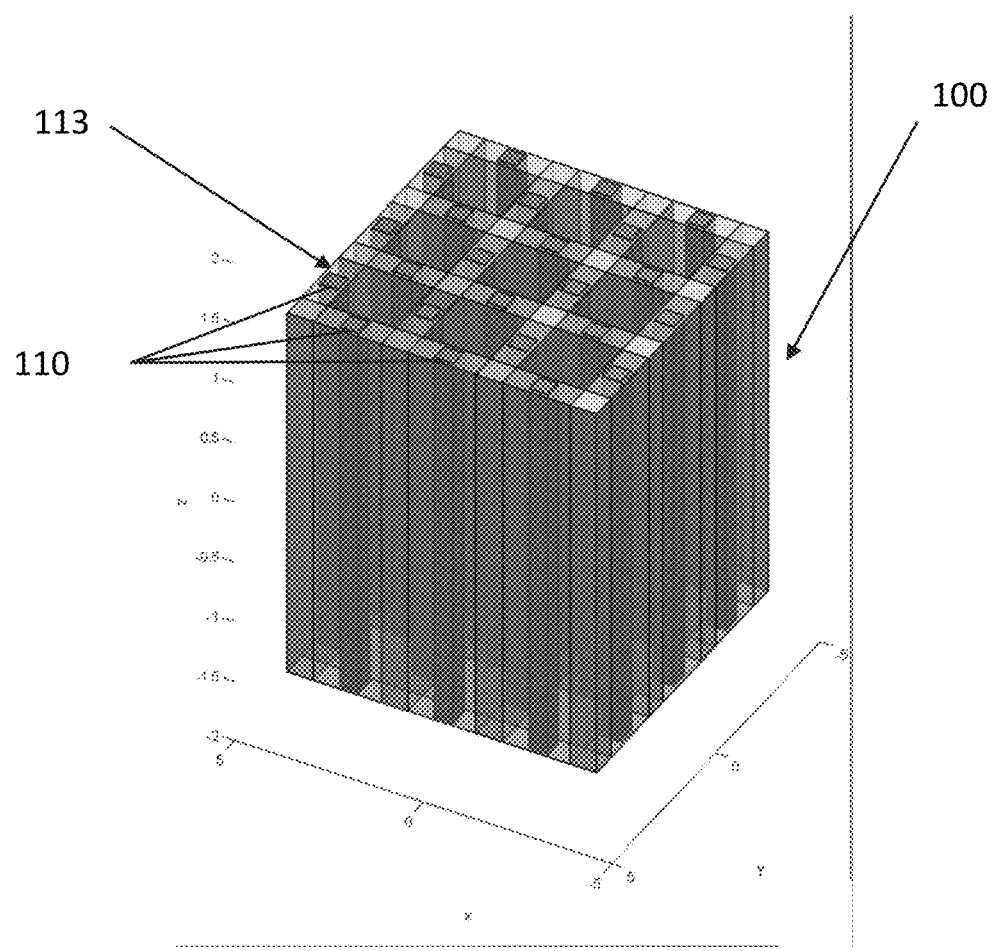
FIG. 8A illustrates another embodiment of the NMR sensor.
Figure 8B:
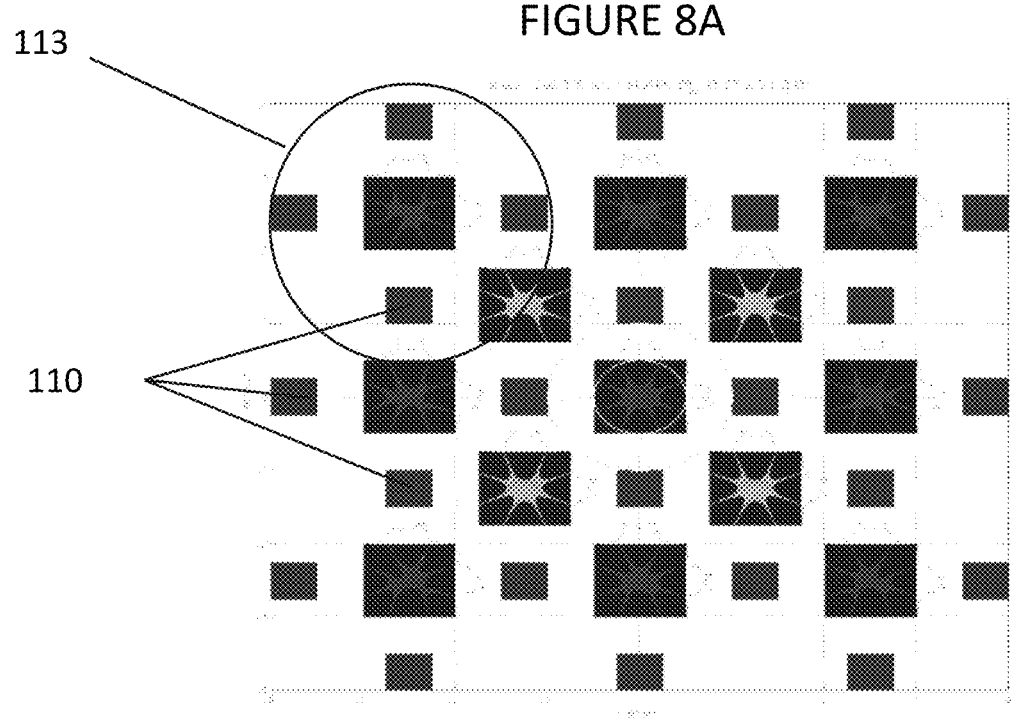
FIG. 8B illustrates the predicted sweet spots of an embodiment of the NMR sensor from FIG. 8A from a computer simulation.

The distance between the center of the detector and the four nearest magnets is d, and the magnets lie on a grid with spacing 2d. As shown in FIG. 1C, each magnet 110 lies at a point (a*d, b*d), where one of the coefficients {a,b} is odd and the other is even. The convention is adopted that all magnets with odd a have positive magnetization $m=+m\hat{x}$, while those with even a have negative magnetization $m=-m\hat{x}$ (this can be achieved in practice by rotating the orientation of the appropriate magnets by 180 degrees).

From Equation (1), the field at the origin due to the magnet at (a*d,b*d) is given by:

$$B(a, b) = \frac{(-1)^b m \mu_0}{4\pi d^3 (a^2+b^2)^{5/2}}\{[3a^2 - (a^2+b^2)]\hat{x} - 3ab\hat{y}\}. \qquad (2)$$

In Equation (2), $\mu_0$ is the permeability of free space (or vacuum permeability), with an SI value of $\mu_0=4\pi\times10^{-7}$ N/A². Due to symmetry, the total $\hat{y}$ component due to the entire grid cancels, as does the $(a^2+b^2)$ term of the $\hat{x}$ component. The total field at the origin due to the infinite grid shown in FIG. 1C is then:

$$B = \frac{3 m \mu_0}{4\pi d^3} \sum_{j=-\infty}^{\infty}\sum_{k=-\infty}^{\infty} \frac{(2j+1)^2 - (2k)^2}{[(2j+1)^2 - (2k)^2]^{5/2}}\hat{x} \qquad (3)$$

$$B \approx \frac{0.44\, m\mu_0}{d^3}\hat{x}. \qquad (4)$$

Note that this is a simplification. For a magnet of characteristic length l located at a distance r from the origin, the assumption of a point dipole in Equation (1) is valid only if the magnet is located far enough away such that l<<r. The field experienced due to magnets located closer than this must be calculated by treating the magnets as three-dimensional objects of finite size and integrating over their volumes. Since the magnetic field falls off as $1/r^3$, nearby magnets contribute most of the total field, and so the error in Equation (4) is significant. Nevertheless, it generally gives the correct order of magnitude for the total field and can be used for basic considerations.

Different embodiments of the NMR sensor 100 (MultiSPOT) can use each individual sweet spot for analysis of a different sample (which may be rock, fluid, etc.), and depending on the pattern of the arrays 113, the samples may have approximately the same magnetic resonance frequency. Depending on the availability of the necessary electronics (e.g. NMR console, radiofrequency (RF) power amplifier, and tuning circuit), multiple samples can therefore be measured simultaneously. In another embodiment, multiple samples can be measured sequentially. The latter method would solve the problem of low duty cycle in conventional low-field measurements; each sample can be analyzed in turn while the others repolarize. In an embodiment, this may be accomplished by using a q-switch for each circuit. Q-switching is a technique designed to shorten the ringing time of the pulsed NMR transmission/acquisition circuit by dynamically adjusting the impedance of the receiver and the probe during pulsing and signal acquisition. Here, the same technique can be used to dynamically select the signal only from the desired probe for detection by the receiver. The technique can also be used to dynamically select which probe applies pulses at any given time. However, any method or hardware could be used to select between the probes in order to sequentially measure the different samples. The simultaneous method would require one set of electronics for each sample, while the sequential method could potentially reduce this number by a factor of up to 1/d, where d is the duty cycle of the measurement (e.g., a factor of 10 for a duty cycle of 10%). Note that one advantage of low duty cycle is that it reduces the extent of heating in the electronic circuit, and so high duty cycle might require additional engineering to prevent overheating.

In addition to measurements of static samples, there are also some compelling applications of the MultiSPOT design for analysis of moving fluids. NMR can be used to measure the fluid velocity, acceleration, and higher order derivatives, and can be used for characterization of flow. The MultiSPOT can be used for this purpose, but since the individual units make independent, localized measurements of the fluid passing through them, the device can form a mesh that maps the fluid velocity (or acceleration, or any other time-derivative of position) as a function of location along the flow cross-section. The MultiSPOT can thus be used for resolved imaging (potentially at high spatial resolution, depending on the size of the units) of flow, turbulence, etc. inside of a tube or pipe. A region of strong (but not necessarily homogeneous) magnetic field can be created upstream of the MultiSPOT device using some other arrangement of magnets, in order to polarize the nuclear spins of the fluid before they reach the device. Other measurements which may be analyzed with the MultiSPOT may include without limitation, a composition of the fluid sample, a water cut of the fluid sample, one or more molecular weights of any hydrocarbons contained within the fluid sample, or combinations thereof.

The MultiSPOT can also be used to increase the total flow length along which an NMR measurement can be made. In situations where the size (i.e., outer diameter) of the tubing is comparable to the size (i.e., inner diameter) of the unit cell, the flow path can simply be threaded among the different units. The total flow path can thus be increased, potentially indefinitely (although in practice, this will be restricted by the size of the MultiSPOT device), while the fraction of that path lying outside the magnet sweet spots can be minimized. This can dramatically increase the polarization time, especially in situations of fast flow.

Figure 9:
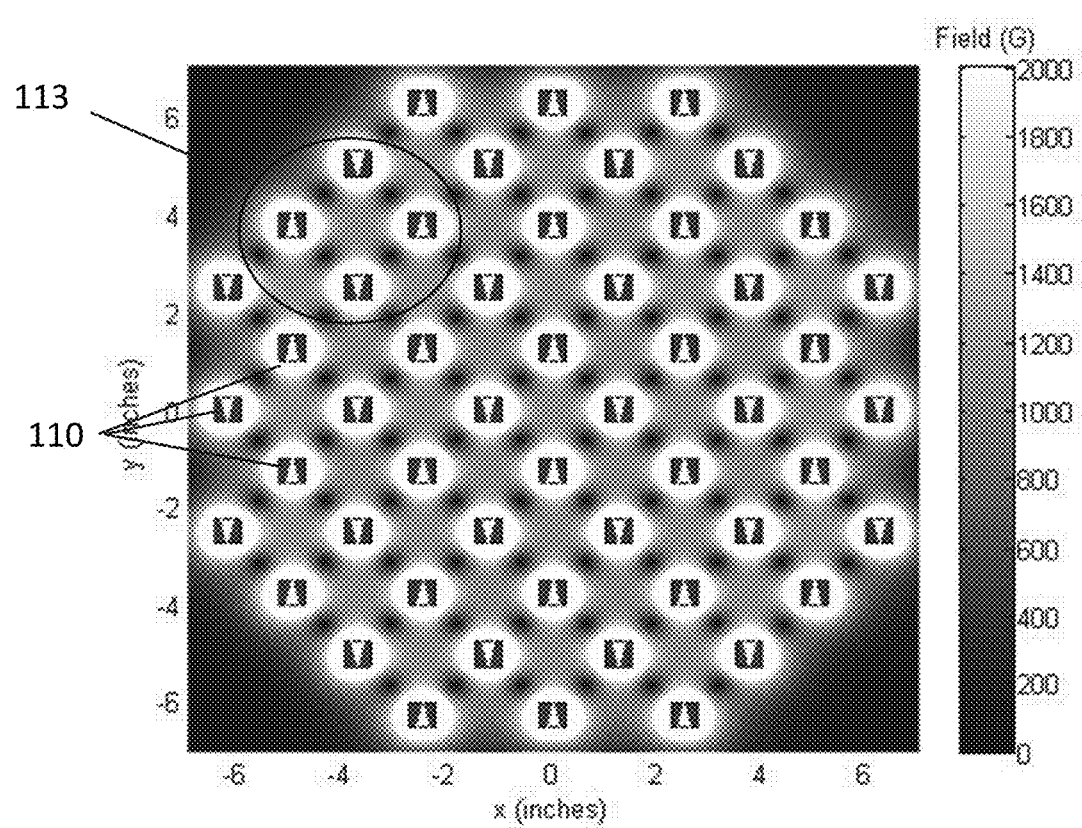
FIG. 9 illustrates a computer simulation of the magnetic field strength, B, and the predicted sweet spots from an embodiment of the NMR sensor with 52 magnets.

FIG. 9 shows the arrangement that maximizes the number of arrays 113 for a given number of magnets 110, in the case of a four-magnet array 113. This arrangement minimizes the surface-to-area ratio of its outside border; in principle the optimal design would have a perfectly circular border. FIG. 9 shows an arrangement which is an approximation to that shape. The example shown features 37 arrays made of 52 magnets, much higher than the 1:4 ratio of a single unit; this ratio further increases as the sensor gets larger. Other embodiments of sensor 100 may contain any suitable number of arrays 113 and magnets 110 depending on cost and application. Although not obvious in FIG. 9, the sweet spots are distorted near the edges (this can be seen in FIG. 8B). In an embodiment, the outer units can be used for pre-polarization in a flow experiment (polarization requires only a strong magnetic field, not a homogeneous one), while the inner units are used for the NMR measurement itself. In the most extreme case, only the most central unit can be used for a short NMR experiment while all other units are used for pre-polarization, maximizing the available polarization time.

In general, care needs to be taken that the fluid does not flow through a point of zero magnetic field while in transit between different units, as this causes the spins to depolarize. However, in some applications this effect can be taken advantage of; for instance, a measurement (one example being a measurement of polarization time, or "T1") can include steps where the spins are purposely depolarized at a point of zero field while in transit between units.

The NMR measurement can also be split between different sensing regions. For example, NMR remote detection separates an NMR flow experiment into encoding and detection steps that occur at different locations. With a MultiSPOT, those locations can be different sensing units. The flow might occur in the "threaded" configuration described above. Another possibility is that the flow might occur between separate MultiSPOT meshes located at different points along the flow path. Information encoded at one or more particular units at an upstream mesh may disperse and be detected at a number of units in a downstream mesh, allowing for that dispersion to be characterized in addition to any other data provided by the NMR measurement.

Samples which can be analyzed using a MultiSPOT device are not limited to only those of interest to the oil industry (such as petroleum, brine, and natural gas), but also may be samples used in other industrial applications (e.g. food or chemical industry). In other words, static samples do not need to be contained in a rock, and fluids (whether in static or flow configuration) are not limited to water and hydrocarbons; any fluid and/or solid phase material containing NMR-active nuclei may be detected, so long as the electronics are appropriately tuned to the resonance frequency(ies) of the nucleus (i) (1H, 13C, 23Na, etc.) as determined by the magnetic field strength in the sweet spots of the various sensing regions. The sample may be a core sample which is made up of solid phase materials (e.g. rocks, minerals) and fluids (e.g. hydrocarbons, gases) trapped within the pore spaces of the core sample. In a non-oil and gas example, blood may be analyzed to monitor for disease. A measurement may involve more than one nuclear species when appropriate for the sample, which requires either adjusting the frequency at which the electronics are tuned, or else having multiple electronic circuits each dedicated to a particular nucleus.

Figure 10:
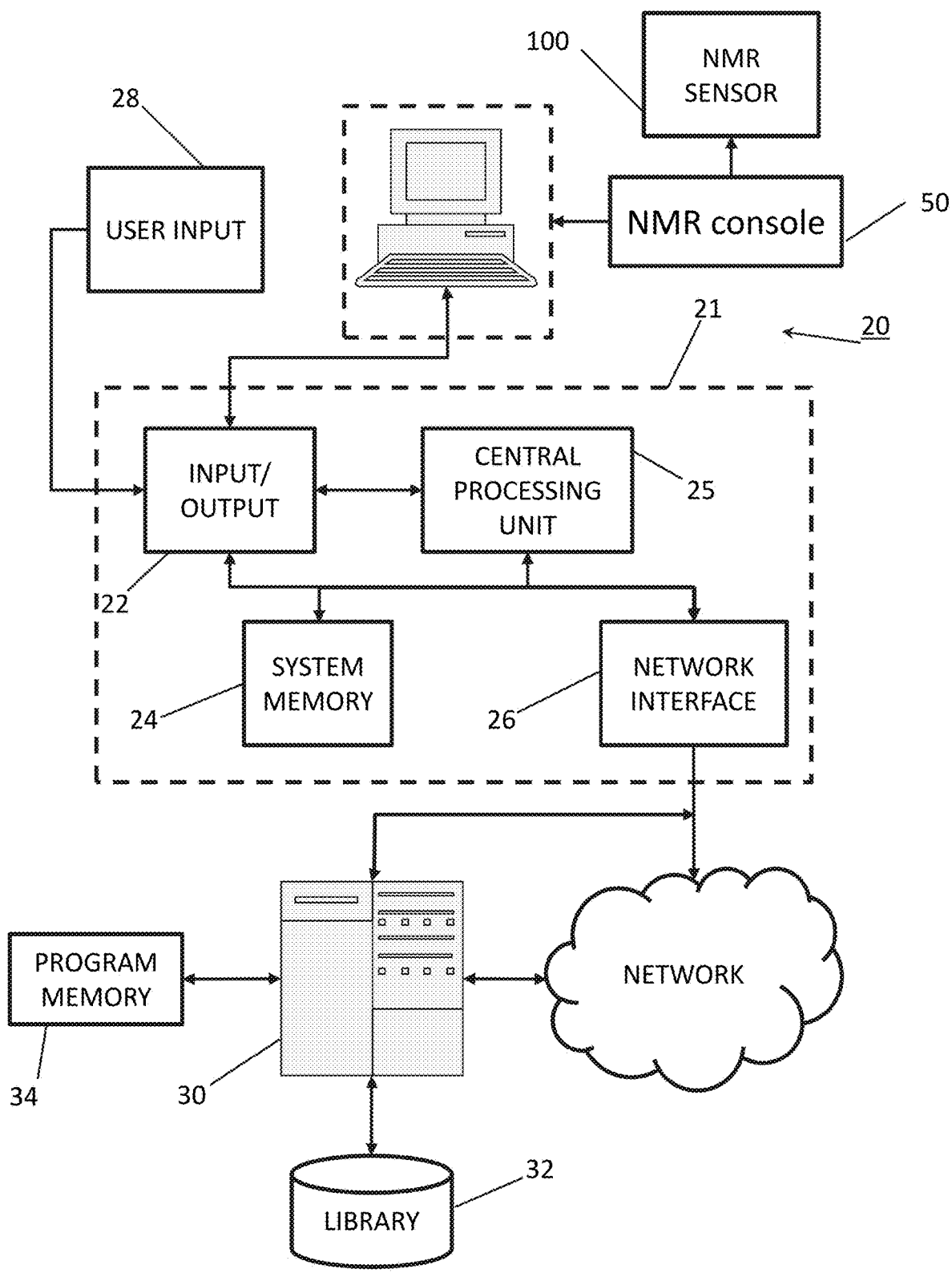
FIG. 10 illustrates a schematic of a computer system which may be used with embodiments of the NMR sensor.
Figure 11:
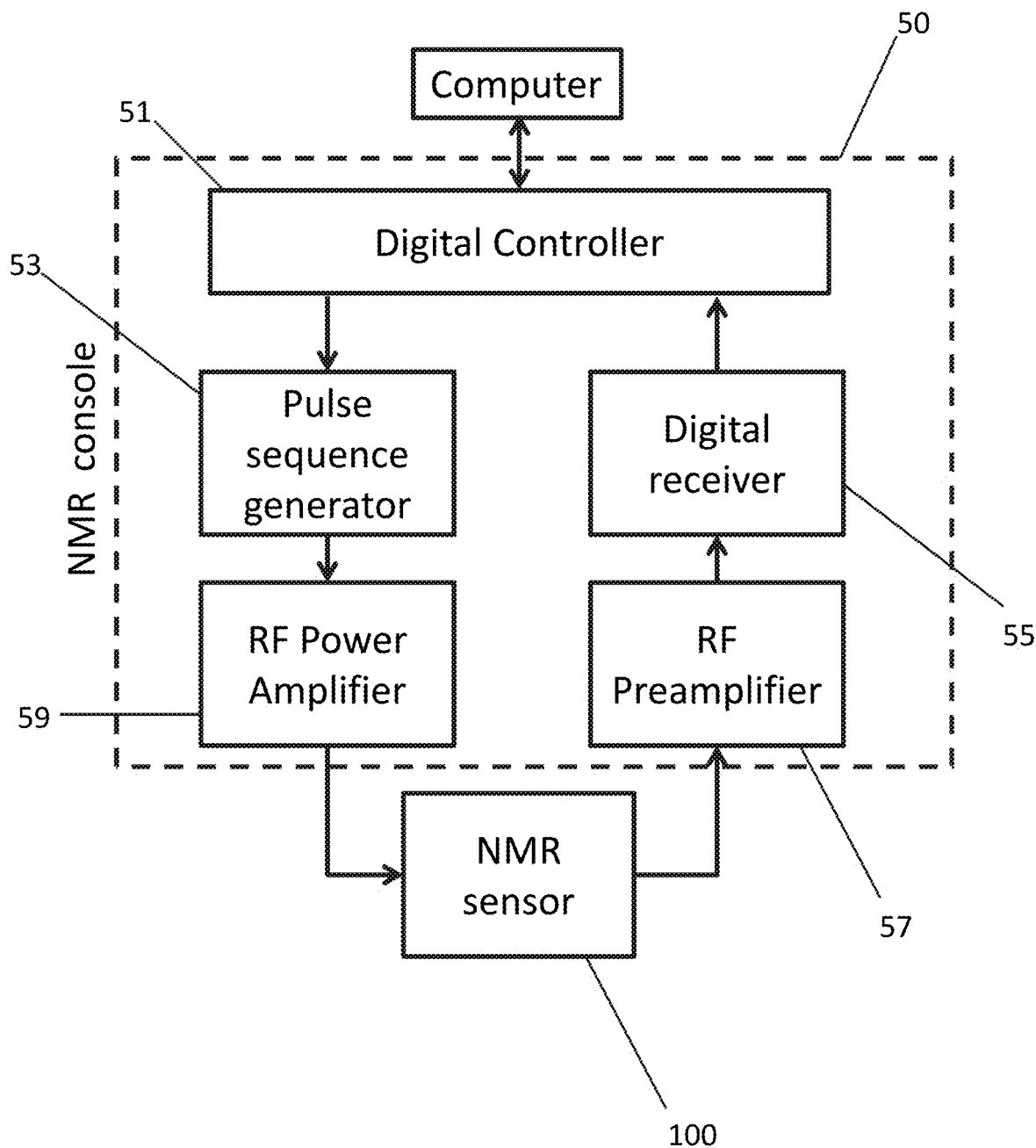
FIG. 11 illustrates a schematic of an NMR console which may be used with embodiments of the NMR sensor.

FIG. 10 illustrates, according to an example of an embodiment of a system 20, which may perform the operations described in this specification to perform the operations disclosed in this specification. In this example, system 20 is as realized by way of a computer system including an NMR sensor 100 connected to a workstation 21 which may be connected to server 30 by way of a network. In an embodiment, NMR sensor 100 may be coupled to an NMR console 50, which also may be coupled to a system 20. FIG. 11 illustrates an NMR console 50 which may be used in conjunction with embodiments of the sensor. NMR console 50 may include without limitation, a digital controller 51, a pulse sequence generator 53, a digital receiver 55, RF power amplifier 59 and an RF preamplifier 57. Other components as are known to those of skill in the art may be included in the NMR console. Although one configuration of an NMR console is shown in FIG. 11, any NMR consoles known to those of skill in the art may be used.

Of course, the particular architecture and construction of a computer system or NMR console 50 useful in connection with this invention can vary widely. For example, system 20 may be realized by a single physical computer, such as a conventional workstation or personal computer, or alternatively by a computer system implemented in a distributed manner over multiple physical computers. Accordingly, the generalized architecture illustrated in FIG. 10 is provided merely by way of example.

As shown in FIG. 10 and as mentioned above, system 20 may include workstation 21, NMR sensor 100 and server 30. Workstation 21 includes central processing unit 25, coupled to system bus. Also coupled to system bus is input/output interface 22, which refers to those interface resources by way of which peripheral functions (e.g., keyboard, mouse, display, etc.) interface with the other constituents of workstation 21. Central processing unit 25 refers to the data processing capability of workstation 21, and as such may be implemented by one or more CPU cores, co-processing circuitry, and the like. The particular construction and capability of central processing unit 25 is selected according to the application needs of workstation 21, such needs including, at a minimum, the carrying out of the functions described in this specification, and also including such other functions as may be executed by computer system. In the architecture of allocation system 20 according to this example, system memory 24 is coupled to system bus, and provides memory resources of the desired type useful as data memory for storing input data and the results of processing executed by central processing unit 25, as well as program memory for storing the computer instructions to be executed by central processing unit 25 in carrying out those functions. Of course, this memory arrangement is only an example, it being understood that system memory 24 may implement such data memory and program memory in separate physical memory resources, or distributed in whole or in part outside of workstation 21. In addition, as shown in FIG. 10, parameter inputs 28 may be input via input/output function 22, and stored in a memory resource accessible to workstation 21, either locally or via network interface 26.

Network interface 26 of workstation 21 is a conventional interface or adapter by way of which workstation 21 accesses network resources on a network. As shown in FIG. 10, the network resources to which workstation 21 has access via network interface 26 includes server 30, which resides on a local area network, or a wide-area network such as an intranet, a virtual private network, or over the Internet, and which is accessible to workstation 21 by way of one of those network arrangements and by corresponding wired or wireless (or both) communication facilities. In this embodiment of the invention, server 30 is a computer system, of a conventional architecture similar, in a general sense, to that of workstation 21, and as such includes one or more central processing units, system buses, and memory resources, network interface functions, and the like. According to this embodiment of the invention, server 30 is coupled to program memory 34, which is a computer-readable medium that stores executable computer program instructions, according to which the operations described in this specification are carried out by allocation system 30. In this embodiment of the invention, these computer program instructions are executed by server 30, for example in the form of a "web-based" application, upon input data communicated from workstation 21, to create output data and results that are communicated to workstation 21 for display or output by peripherals P in a form useful to the human user of workstation 21. In addition, library 32 is also available to server 30 (and perhaps workstation 21 over the local area or wide area network), and stores such archival or reference information as may be useful in allocation system 20. Library 32 may reside on another local area network, or alternatively be accessible via the Internet or some other wide area network. It is contemplated that library 32 may also be accessible to other associated computers in the overall network.

The particular memory resource or location at which the measurements, library 32, and program memory 34 physically reside can be implemented in various locations accessible to allocation system 20. For example, these data and program instructions may be stored in local memory resources within workstation 21, within server 30, or in network-accessible memory resources to these functions. In addition, each of these data and program memory resources can itself be distributed among multiple locations. It is contemplated that those skilled in the art will be readily able to implement the storage and retrieval of the applicable measurements, models, and other information useful in connection with this embodiment of the invention, in a suitable manner for each particular application.

According to this embodiment, by way of example, system memory 24 and program memory 34 store computer instructions executable by central processing unit 25 and server 30, respectively, to carry out the disclosed operations described in this specification, for example, by way of which the NMR data is processed and/or analyzed. These computer instructions may be in the form of one or more executable programs, or in the form of source code or higher-level code from which one or more executable programs are derived, assembled, interpreted or compiled. Any one of a number of computer languages or protocols may be used, depending on the manner in which the desired operations are to be carried out. For example, these computer instructions may be written in a conventional high level language, either as a conventional linear computer program or arranged for execution in an object-oriented manner. These instructions may also be embedded within a higher-level application. Such computer-executable instructions may include programs, routines, objects, components, data structures, and computer software technologies that can be used to perform particular tasks and process abstract data types. The instructions may include software and/or code for running NMR console 50. It will be appreciated that the scope and underlying principles of the disclosed methods are not limited to any particular computer software technology. For example, an executable web-based application can reside at program memory 34, accessible to server 30 and client computer systems such as workstation 21, receive inputs from the client system in the form of a spreadsheet, execute algorithms modules at a web server, and provide output to the client system in some convenient display or printed form. It is contemplated that those skilled in the art having reference to this description will be readily able to realize, without undue experimentation, this embodiment of the invention in a suitable manner for the desired installations. Alternatively, these computer-executable software instructions may be resident elsewhere on the local area network or wide area network, or downloadable from higher-level servers or locations, by way of encoded information on an electromagnetic carrier signal via some network interface or input/output device. The computer-executable software instructions may have originally been stored on a removable or other non-volatile computer-readable storage medium (e.g., a DVD disk, flash memory, or the like), or downloadable as encoded information on an electromagnetic carrier signal, in the form of a software package from which the computer-executable software instructions were installed by allocation system 20 in the conventional manner for software installation.

While the embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A three-dimensional nuclear magnetic resonance (NMR) sensor comprising:
    a plurality of magnet arrays forming the three-dimensional NMR sensor to receive a sample wherein each magnet array comprises a plurality of magnets arranged in a semi-Halbach configuration in which the magnets define a regular or irregular polygon, and wherein the polygons of the magnet arrays form a tessellating pattern in which the magnet arrays each share at least one magnet with another one of the magnet arrays, wherein each semi-Halbach configuration produces a magnetic field both inside and outside of the array, wherein the magnetic field inside each magnet array comprises a sweet spot configured to receive a sample, wherein each sweet spot is a local extremum in magnetic field strength, and wherein the magnets are non-contiguous to one another.

2. The sensor of claim 1, wherein each magnet comprises a permanent magnet.

3. The sensor of claim 1, wherein the magnets each comprise a cuboidal geometry, a cylindrical geometry, or combinations thereof.

4. The sensor of claim 1, further comprising one or more support elements coupled to the arrays.

5. The sensor of claim 1, wherein two or more arrays comprise more than one pattern of magnets.

6. The sensor of claim 1, wherein the arrays are disposed on a flat plane.

7. The sensor of claim 1, wherein the arrays are disposed on a curved plane.

8. The sensor of claim 1, wherein all of the magnets comprise a magnetic field and the magnetic fields are parallel to one another.

9. The sensor of claim 1, wherein at least one of the arrays meets a $4\pi$ Halbach condition.

10. The sensor of claim 1, further comprising one or more coils coupled to each array.

11. The sensor of claim 10, wherein the coils comprise one or more radiofrequency (RF) coils, one or more gradient coils, one or more shimming coils, or combinations thereof.

12. The sensor of claim 11, further comprising one or more switches coupled to each magnet array, wherein the switches are used to select between the coils coupled to each magnet array.

13. A system for using nuclear magnetic resonance (NMR) to analyze a sample from a subsurface formation comprising:
    a three-dimensional NMR sensor comprising a plurality of magnet arrays forming the three-dimensional NMR sensor to receive a sample from a subsurface formation, wherein each magnet array comprises a plurality of magnets arranged in a semi-Halbach configuration in which the magnets define a regular or irregular polygon, and wherein the polygons of the magnet arrays form a tessellating pattern in which the magnet arrays each share at least one magnet with another one of the magnet arrays, wherein each semi-Halbach configuration produces a magnetic field both inside and outside of the array, wherein the magnetic field inside each magnet array comprises a sweet spot configured to receive a sample, wherein each sweet spot is a local extremum in magnetic field strength, and wherein the magnets are non-contiguous to one another;
    an interface for receiving one or more user inputs;
    a memory resource;
    input and output functions for presenting and receiving communication signals to and from a human user;
    one or more central processing units for executing program instructions coupled to the three-dimensional NMR sensor and configured to receive one or more signals from the three-dimensional NMR sensor; and
    program memory, coupled to the central processing unit, for storing a computer program including program instructions that, when executed by the one or more central processing units, cause the system to perform a plurality of operations for analyzing the sample from the subsurface formation.

14. The system of claim 13, further comprising an NMR console coupled to the NMR sensor.

15. The system of claim 13, further comprising one or more coils coupled to each array.

16. The system of claim 15, wherein the coils comprise one or more radiofrequency (RF) coils, one or more gradient coils, one or more shimming coils, or combinations thereof.

17. The system of claim 16, further comprising one or more switches coupled to each magnet array, wherein the switches are used to select between the coils coupled to each magnet array.

18. A method of using nuclear magnetic resonance (NMR) to analyze a sample from a subsurface formation comprising:
    a) disposing a sample extracted from a subsurface formation within a three-dimensional NMR sensor, the three-dimensional NMR sensor comprising:
        a plurality of magnet arrays forming the three-dimensional NMR sensor to receive the sample, wherein each magnet array comprises a plurality of magnets arranged in a semi-Halbach configuration in which the magnets define a regular or irregular polygon, and wherein the polygons of the magnet arrays form a tessellating pattern in which the magnet arrays each share at least one magnet with another one of the magnet arrays, wherein each semi-Halbach configuration produces a magnetic field both inside and outside of the array, wherein the magnetic field inside each magnet array comprises a sweet spot configured to receive a sample, wherein each sweet spot is a local extremum in magnetic field strength, and wherein the magnets are non-contiguous to one another; and
    b) using the three-dimensional NMR sensor to analyze the sample.

19. The method of claim 18, wherein the sample is a core sample comprising a solid phase.

20. The method of claim 19, wherein (b) comprises using the NMR sensor to analyze a fluid within the core sample.

21. The method of claim 19, wherein (b) comprises using the NMR sensor to analyze the solid phase of the core sample.

22. The method of claim 18, further comprising disposing a plurality of samples within the plurality of magnet arrays and analyzing each sample simultaneously.

23. The method of claim 18, further comprising disposing a plurality of samples within the plurality of magnet arrays and analyzing each sample sequentially.

24. The method of claim 18, wherein (b) comprises using the NMR sensor to determine at least one of a porosity of the sample, a saturation of the sample, a permeability of the sample, a chemical composition of the sample, a chemical shift of the sample, a pore size distribution of the sample, one or more molecular weights of any hydrocarbons contained within the sample, relaxation times of the sample, diffusion coefficients of the sample, or combinations thereof.

25. A method of using nuclear magnetic resonance (NMR) to analyze a fluid sample from a subsurface formation comprising:
    a) flowing a fluid sample extracted from a subsurface formation through a three-dimensional NMR sensor, the three-dimensional NMR sensor comprising:
        a plurality of magnet arrays forming the three-dimensional NMR sensor to receive the fluid sample, wherein each magnet array comprises a plurality of magnets arranged in a semi-Halbach configuration in which the magnets define a regular or irregular polygon, and wherein the polygons of the magnet arrays form a tessellating pattern in which the magnet arrays each share at least one magnet with another one of the magnet arrays, wherein each semi-Halbach configuration produces a magnetic field both inside and outside of the array, wherein the magnetic field inside each magnet array comprises a sweet spot configured to receive a sample, wherein each sweet spot is a local extremum in magnetic field strength, and wherein the magnets are non-contiguous to one another; and b) using the three-dimensional NMR sensor to analyze the fluid sample.

26. The method of claim 25, wherein (a) comprises flowing the fluid sample through one or more NMR sensors.

27. The method of claim 26, further comprising flowing fluid samples through each NMR sensor and analyzing each fluid sample simultaneously.

28. The method of claim 25, wherein (b) comprises using the NMR sensor to determine one of a composition of the fluid sample, a water cut of the fluid sample, one or more molecular weights of any hydrocarbons contained within the fluid sample, or combinations thereof.

29. The method of claim 25, wherein (b) comprises using the NMR sensor to create a visualization of a flow of the fluid sample.

30. The method of claim 25, wherein (b) comprises measuring one or more flow characteristics of the fluid sample.

31. The method of claim 30, wherein the one or more flow characteristics comprises velocity, acceleration, or combinations thereof.

* * * * *